United States Patent
Fiorentino et al.

(10) Patent No.: US 7,718,811 B2
(45) Date of Patent: May 18, 2010

(54) OXIDATION PROCESS IN FLUIDISED BED REACTOR

(75) Inventors: Michele Fiorentino, Aix en Provence (FR); David Newton, Farnham (GB); George Fredrick Salem, Aurora, IL (US); Bruce Leo Williams, East Yorkshire (GB)

(73) Assignee: Ineos Europe Limited, Hampshire (GB)

( * ) Notice: Subject to any disclaimer, the term of this patent is extended or adjusted under 35 U.S.C. 154(b) by 0 days.

(21) Appl. No.: 12/155,336

(22) Filed: Jun. 3, 2008

(65) Prior Publication Data

US 2009/0030225 A1    Jan. 29, 2009

Related U.S. Application Data

(60) Continuation of application No. 11/541,678, filed on Oct. 3, 2006, now abandoned, which is a continuation of application No. 11/239,137, filed on Sep. 30, 2005, now Pat. No. 7,189,871, which is a division of application No. 10/303,769, filed on Nov. 26, 2002, now Pat. No. 7,145,033.

(51) Int. Cl.
    C07D 307/36    (2006.01)
    C07C 67/00    (2006.01)
(52) U.S. Cl. .................................. 549/262; 560/241
(58) Field of Classification Search ................ None
    See application file for complete search history.

(56) References Cited

U.S. PATENT DOCUMENTS

| 3,987,118 A | 10/1976 | Kuck |
| 4,102,914 A | 7/1978 | Beuther et al. |

FOREIGN PATENT DOCUMENTS

| CA | 2 297 428 A1 | 1/2000 |
| DE | 1571 39 | 10/1982 |
| EP | 0 672453 A2 | 9/1995 |
| EP | 0 685 449 A1 | 12/1995 |
| EP | 0 832 877 A2 | 4/1998 |
| EP | 0 985 655 A1 | 3/2000 |
| EP | 1 043 064 A2 | 10/2000 |
| EP | 1 043 064 A3 | 12/2001 |
| EP | 1 043 064 B1 | 6/2004 |
| EP | 0 985 655 B1 | 8/2004 |
| WO | WO 97/39300 | 10/1997 |
| WO | WO 99/51339 | 10/1999 |

OTHER PUBLICATIONS

Fakeeha et al, Chemical Engineering and Processing, Model of a Circulating Fluidized Bed for Ammoxidation of Propane to Acrylonitrile, 2000, 39, pp. 161-170.*
Chaouki et al, Korean Journal of Chemical Engineering, Selective and Complete Catalytic Oxidation of Natural Gas in Turbulent Fluidized Beds, 1999, 16(4), pp. 494-500.*
Fei, et al.; A CFB Reactor Model for the Synthesis of Acrylonitrile; 1998; (Dept. of Chemical Engineering, Tsinghua University, Beijing 100084) pp. 276-281; abstract.
Hebisch, et al; "Turbulent bed reactor for highly exothermic reactions . . . aqueous stationary components"; DD-157139; 1983-20130K; abstract.
Wang, et al; "Study on the turbulent fluidized-bed reactor for vinyl acetate production in commercial scale"; 123:9973; abstract.
Wei, et al.; "Circulating fluidized bed reactor model for the synthesis of acrylonitrile"; 128:321967; abstract.
Zhanwen, et al; "Industrial Trial of a Vinyl Acetate Synthesis Turbulent Fluidised Bed Reactor"; Chemical Reaction Engineering and Technology; vol. 11, No. 1, Mar. 1995; 6 pages.

* cited by examiner

*Primary Examiner*—Paul A Zucker
(74) *Attorney, Agent, or Firm*—Nixon & Vanderhye

(57) ABSTRACT

A process for reacting in a fluid bed reactor at least one oxidisable reactant with molecular oxygen in the presence of a catalytically active fluidised bed of solid particles. In the process a molecular oxygen-containing gas having an oxygen concentration greater than that of air is introduced into the fluidised bed whilst the fluidised bed is maintained in a turbulent regime. The process is suitable for oxidation, ammoxidation and carboxylation processes, including the production of maleic anhydride, acrylonitrile, ethylene, acetic acid and vinyl acetate.

22 Claims, 4 Drawing Sheets

OXIDATION PROCESS IN FLUIDISED BED REACTOR

CROSS-REFERENCES TO RELATED APPLICATIONS

This application is a continuation of application Ser. No. 11/541,678, filed Oct. 3, 2006, now abandoned, which is a continuation of application Ser. No. 11/239,137, filed Sep. 30, 2005, now U.S. Pat. No. 7,189,871, which is a divisional of application Ser. No. 10/303,769, filed Nov. 26, 2002, now U.S. Pat. No. 7,145,033, the entire content of which is hereby incorporated by reference in this application.

The present invention relates to a process for reacting at least one oxidisable reactant with molecular oxygen and in particular to reaction in a fluid bed reactor.

BACKGROUND OF THE INVENTION

Reactions of molecular oxygen with oxidisable reactants in the presence of fluidised beds of catalyst are known. For example, the acetoxylation of ethylene to produce vinyl acetate by reaction of acetic acid, ethylene and an oxygen-containing gas in a fluid bed reactor is known from EP-A-0672453, EP-A-0685449 and EP-A-0847982. The reaction of oxygen with ethane to produce acetic acid in a fluid bed reactor is known from EP-A-0546677.

EP-A-0685449 discloses a process for manufacturing vinyl acetate in a fluid bed reactor comprising feeding ethylene and acetic acid into the fluid bed reactor through one or more inlets, feeding an oxygen-containing gas into the fluid bed reactor through at least one further inlet, co-joining the oxygen-containing gas, ethylene and acetic acid in the fluid bed reactor while in contact with a fluid bed catalyst material to enable the ethylene, acetic acid and oxygen to react to produce vinyl acetate and recovering the vinyl acetate from the fluid bed reactor. According to EP-A-0685449, the oxygen may be added in pure form or as an admixture with inert gas such as nitrogen or carbon dioxide. Since the oxygen and hydrocarbons are not mixed until they are both inside the reactor, catalyst is present when they meet and reaction proceeds immediately, causing the oxygen partial pressure to drop. Thus, an advantage of feeding an oxygen-containing gas to the reactor through at least one further inlet in addition to the ethylene and acetic acid reactants is that it allows significantly higher levels of oxygen to be safely employed without a high inventory of flammable gas mixtures.

Bubbling bed operation is not appropriate for reactions using molecular oxygen-containing gas because of the possibility of a plume or bubbles of oxygen forming in the bed, which can be unsafe.

There remains a need for an improved fluid bed process in which molecular oxygen is reacted with at least one oxidisable reactant.

SUMMARY OF THE INVENTION

It has now been found that if a molecular oxygen-containing gas having an oxygen concentration greater than that of air is to be fed into a fluidised bed comprising catalyst particles in a reactor, the fluidised bed should be maintained in a turbulent regime.

Thus, according to one aspect of the present invention there is provided a process for reacting in a fluid bed reactor, at least one oxidisable reactant with molecular oxygen in the presence of a catalytically active fluidised bed of solid particles in which process a molecular oxygen-containing gas having an oxygen concentration greater than that of air is introduced into said fluidised bed whilst said fluidised bed is maintained in a turbulent regime.

Fluidised beds comprising solid particles may be operated in various regimes—for example, as spouting beds, fast fluidisation (transporting) beds, bubbling beds and turbulent beds etc.

A turbulent regime for a fluidised bed of solid particles is a fluidised bed in which large discrete bubbles or voids are generally absent and the bed is substantially uniform. Clusters and strands of particles move about violently within the bed making for a general lack of distinction between continuous and discontinuous phases in the bed. In a turbulent fluidised bed, the upper surface is considerably more diffuse than in a bubbling bed because of greater freeboard activity.

A turbulent regime has a linear velocity of the fluidising gas (linear gas velocity) which is greater than the transition velocity ($U_k$) which is, the gas velocity at which there is a transition from bubbling to turbulent regimes.

Preferably the ratio of transition velocity ($U_k$) terminal velocity ($U_t$) is in the range 0.1:1 to 25:1. Typically, at a pressure in the range 1 to 30 bara, the ratio $U_k{:}U_t$ may be in the range 0.1:1 to 25:1, preferably in the range 0.3:1 to 13:1. For small solid particles (for example, in the range 30 to 150 microns diameter), the turbulent regime has a transition velocity $U_k$ which is much greater than the terminal velocity ($U_t$) of the mean particle size of bed material. As pressure in the fluid bed is increased, the ratio $U_k{:}U_t$ decreases, for example from 3:1 to 1:1 or from 3.5:1 to 0.5:1.

$U_k{:}U_t$ is greater for smaller particles than for larger particles.

The use of a turbulent fluid bed provides good mass transfer. Thus, one advantage is that large bubbles of molecular oxygen-containing gas are not formed or present in the bed. Therefore, the potential for gas bubbles forming in the bed having a molecular oxygen concentration in an explosive region is reduced which has increased safety implications. Also, at the oxygen injection point, there is reduced tendency for discrete jet or plume formation because of the greater mixing, so the potential for adverse consequences in the event of an ignition is reduced or eliminated. Furthermore, the mixing of a turbulent fluid bed can produce a more homogeneous temperature profile. There is good heat transfer and low tendency for hot spots to form.

The process of the present invention is suitable for the carboxylation of alkenes to produce unsaturated esters by reaction of a carboxylic acid, an olefin and molecular oxygen in the presence of an effective amount of an active catalyst, such as for example the reaction of acetic acid, ethylene and oxygen to produce vinyl acetate.

The process of the present invention is also suitable for the reaction in the presence of an effective amount of an active catalyst, of molecular oxygen with (a) ethane to produce ethylene and/or acetic acid, (b) with ethylene to produce acetic acid and (c) mixtures of ethane and ethylene to produce acetic acid, optionally with ethylene.

The process of the present invention is suitable for the oxidation of hydrocarbons by reaction with a molecular oxygen in the presence of an effective amount of an active catalyst, such as for example the reaction of C4's to produce maleic anhydride.

The process of the present invention is suitable for the ammoxidation of hydrocarbons by reaction with a molecular oxygen and ammonia in the presence of an effective amount of an active catalyst, such as for example the ammoxidation of propene or propane to produce acrylonitrile.

Preferably, the fluid bed comprises solid particles with a relatively broad particle size distribution. Thus, for fluid beds comprising solid particles having a particle diameter in the range 20 to 300 microns, the particle diameter size distribution is preferably at least 20 microns, more preferably at least 50 microns and most preferably at least 100 microns.

Suitably, the fluid bed comprises solid particles having sizes according to one or more of the following independent criteria: (i) at least 65% of the particles have particle diameters in the range 20-120 microns; (ii) less than 15% of the particles have a particle diameter less than 45 microns; and (iii) less than 5% of the particles have a particle diameter greater than 105 microns.

The total linear gas flow through the fluidised bed (also referred to as the superficial velocity) is preferably up to 50 cm/s, more preferably up to 35 cm/s for the reaction of ethane and/or ethylene with oxygen to produce acetic acid and/or ethylene and more preferably up to 30 cm/s for the production of vinyl acetate from ethylene, acetic acid and oxygen.

When the process of the present invention is used for the production of vinyl acetate by the reaction of ethylene and acetic acid with molecular oxygen in a fluid bed reactor in the presence of a catalytically active fluidised bed of solid particles having a particle diameter in the range 20 to 300 microns and having a particle diameter size distribution of at least 20 microns, preferably at least 50 microns and more preferably at least 100 microns, the fluidised bed may be maintained in a turbulent regime by using solid particles having a particle density of at least 0.6 g/cm$^3$ and a settled bed density of at least 0.4 g/cm$^3$ and by operating at a pressure in the fluid bed reactor of at least 4 bara with a total linear gas flow through the fluidised bed of from 2 to 30 cm/s inclusive, preferably 2-25 cm/s inclusive.

Thus, according to one aspect of the present invention there is provided a process for the production of vinyl acetate by the reaction of ethylene and acetic acid with molecular oxygen in a fluid bed reactor in the presence of a catalytically active fluidised bed of solid particles having a particle diameter in the range 20 to 300 microns and having a particle diameter size distribution of at least 20 microns, preferably at least 50 microns and more preferably at least 100 microns, and in which process a molecular oxygen-containing gas having an oxygen concentration greater than that of air is introduced into the fluidised bed, and the fluidised bed is maintained in a turbulent regime by using solid particles having a particle density of at least 0.6 g/cm$^3$ and a settled bed density of at least 0.4 g/cm$^3$ and by operating at a pressure in the fluid bed reactor of at least 4 bara with a total linear gas flow through the fluidised bed of from 2 to 30 cm/s inclusive, preferably 2-25 cm/s inclusive.

Preferably, in such a process for the production of vinyl acetate, the fluid bed comprises catalyst particles which have a particle size distribution in which (i) at least 65% of the particles have particle diameters in the range 20-120 microns, (ii) less than 15% of the particles have a particle diameter of less than 45 microns and (iii) less than 5% of the particles have a particle diameter of greater than 105 microns.

As the linear gas flow rate is increased, so increasingly dense catalyst particles will be required to reduce transportation of catalyst particles from the fluidised bed.

Suitably, the catalyst particles useful for the production of vinyl acetate have a particle density in the range 1.1 to 1.5 g/cm$^3$. The density of the particles may be changed by changing the amount of liquid components such as acetic acid introduced into the fluid bed of catalyst during the process.

When the process of the present invention is used for the reaction of molecular oxygen with (a) ethane to produce ethylene and/or acetic acid, (b) ethylene to produce acetic acid, or (c) mixtures of ethane and ethylene to produce acetic acid, optionally with ethylene, in a fluid bed reactor in the presence of a catalytically active fluidised bed of solid particles having a particle diameter in the range 20 to 300 microns and having a particle diameter size distribution of at least 20 microns, preferably at least 50 microns and more preferably at least 100 microns, the fluidised bed may be maintained in a turbulent regime by using solid particles having a particle density of at least 0.6 g/cm$^3$ and a settled bed density of at least 0.4 g/cm$^3$ and by operating at a pressure in the fluid bed reactor of at least 4 bara with a total linear gas flow through the fluidised bed of from 2 to 35 cm/s, inclusive.

Thus, according to one aspect of the present invention there is provided a process for the reaction of molecular oxygen with (a) ethane to produce ethylene and/or acetic acid, (b) ethylene to produce acetic acid or (c) mixtures of ethane and ethylene to produce acetic acid, optionally with ethylene, in a fluid bed reactor in the presence of a catalytically active fluidised bed of solid particles having a particle diameter in the range 20 to 300 microns and having a particle diameter size distribution of at least 20 microns, preferably at least 50 microns and more preferably at least 100 microns, and in which process a molecular oxygen-containing gas having an oxygen concentration greater than that of air is introduced into the fluidised bed, and the fluidised bed is maintained in a turbulent regime by using solid particles having a particle density of at least 0.6 g/cm$^3$ and a settled bed density of at least 0.4 g/cm$^3$ and by operating at a pressure in the fluid bed reactor of at least 4 bara with a total linear gas flow through the fluidised bed of from 2 to 35 cm/s, inclusive.

Preferably, in such a process for the reaction of ethane and/or ethylene with molecular oxygen to produce ethylene and/or acetic acid, the fluidised bed comprises particles in which (i) at least 65% of the particles have particle diameters in the range 20-120 microns, (ii) less than 15% of the particles have a particle diameter of less than 45 microns and (iii) less than 5% of the particles have a particle diameter of greater than 105 microns.

Suitably, the catalyst particles used for the oxidation of ethane and/or ethylene to produce ethylene and/or acetic acid have a particle density of 1.25 to 3.5 g/cm$^3$, preferably 1.75 to 2.25 g/cm$^3$.

It has been found that such a process according to the present invention for the production of vinyl acetate can be readily scaled up because data obtained on a small scale is applicable to the full scale because both fluid beds operate in a turbulent regime.

In the present invention it has been found that by operating at high pressures (for example at least 4 bara), a turbulent regime may be maintained in the fluid bed with a small amount (for example less than 15%, preferably less than 5%) of solid particles having a particle diameter of less than 45 microns, or even less than 20 microns (fines).

The use of low levels of fines provides an advantage of reduced loss of the particles from the reactor and may thus provide advantages of design of any cyclones to reduce loss of material from the reactor.

In other processes according to the present invention, it may be possible to maintain a turbulent regime in the fluid bed by using a fluid bed comprising solid particles with greater than 15% of the particles having a particle diameter of less than 45 microns, for example 30 to 40% inclusive and at the same time operating at a lower pressure, for example at 0.5 to 1 barg, inclusive and a higher fluidising gas velocity.

The density of the solid particles of the fluid bed may be modified by the use of a densifier during preparation of the particles. Densification of the particles may be achieved by substitution of one or more metals of the catalyst by at least one metal which is of higher atomic weight and, preferably, which is also chemically equivalent, that is, has the same or similar activity and/or selectivity to the substituted metal(s). For example, a catalyst comprising the metals, Mo, V, Nb may be densified by substituting one or more of Mo, V, or Nb by at least one metal of higher atomic weight such as Sn, Sb, Te, La, Ta, W, Re, Pb, Bi, Ce, Pr, Gd and Yb.

Alternatively, the density of the solid particles of the fluid bed may be modified by the use of a fluidising gas, such as ethylene. The fluidising gas may comprise at least 30 mol % ethylene by volume, for example, at least 30 mol % to 85 mol % ethylene.

Increasing the density of the fluid bed solid particles, for example by using a densifier, may enable higher superficial gas velocities to be used and/or higher levels of fines whilst maintaining the fluid bed in a turbulent, non-transporting regime.

The process of the present invention allows for the safe introduction into a fluid bed, of a molecular oxygen-containing gas having an oxygen concentration of up to almost pure molecular oxygen. Suitably, molecular oxygen-containing gases for use in the present invention include oxygen gas with minor amounts of impurities such as argon and nitrogen which each may be present at a concentration of less than 0.1% by volume. The concentration of oxygen in the molecular oxygen-containing gas is suitably in the range greater than 21% to 100%, preferably in the range 50 to 100%, for example a concentration of greater than 99.5% by volume, suitably a concentration of at least 99.6% by volume.

The means for introducing the molecular oxygen-containing gas into the fluidised bed should recognise the hazards which may have to be considered with such materials. Thus, for example, for safety, the inlet(s) for the molecular oxygen-containing gas are preferably located at a distance from the catalyst support means of greater than any potential flame length. The potential flame length is determined by factors such as the inlet pipe diameter and inlet gas velocity. The inlets should be positioned and inlet pressures and velocities selected, so that the molecular oxygen-containing gas is dispersed and mixed in the region of the inlet. The inlets should be positioned not too close to the reactor walls, in case there is a shock wave following a detonation. The inlets should be positioned so that the molecular oxygen-containing gas does not impinge directly on surfaces or other structures in the reactor such as inlets for other reactants.

In the process of the present invention the at least one oxidisable reactant may be introduced into the fluidised bed as a gas and/or liquid through one or more inlets.

One or more gaseous reactants may be introduced into the fluidised bed together with or preferably at least in part, separately from, the molecular oxygen-containing gas.

This gaseous reactant may be introduced as a component of the fluidising gas. The fluidising gas may comprise fresh gaseous reactants and/or recycle gases. The gaseous reactant introduced into the reactor may be ethylene which may be used with acetic acid to produce vinyl acetate. The gaseous reactant introduced into the reactor may be ethane and/or ethylene which may be oxidised respectively to ethylene and/or acetic acid and to acetic acid.

Ethylene used in the process of the present invention may be used in substantially pure form or admixed with one or more of nitrogen, methane, ethane, carbon dioxide and water in the form of steam or one or more of hydrogen, $C_3/C_4$ alkenes or alkanes. Ethane used in the process of the present invention may be used in substantially pure form or admixed with one or more of nitrogen, methane, ethylene, carbon dioxide and water in the form of steam or one or more of hydrogen, $C_3/C_4$ alkenes or alkanes.

The process of the present invention may suitably be operated at a temperature from 100 to 500° C., preferably 140 to 400° C. The process may suitably be operated at a pressure of 10 to 3000 kPa gauge (0.1 to 30 barg), preferably 20 to 2500 Pa gauge (0.2 to 25 barg).

The fluidised bed may comprise catalyst particles and optionally catalytically inactive particles. The catalyst may be any suitable fluidisable catalyst. The catalyst may be a supported catalyst. Suitable catalyst supports include porous silica, alumina, silica/alumina, titania, silica/titania, zirconia and mixtures thereof. Preferably, the support is silica.

A typical catalyst composition useful in this invention, may have the following particle size distribution:—

| | |
|---|---|
| 0 to 20 microns | 0-30 wt % |
| 20 to 44 microns | 0-60 wt % |
| 44 to 88 microns | 10-80 wt % |
| 88 to 106 microns | 0-80 wt % |
| >106 microns | 0-40 wt % |
| >300 microns | 0-5 wt % |

Persons skilled in the art will recognise that support particles sizes of 44, 88, 106 and 300 microns are arbitrary measures in that they are based on standard size ranges such as may be measured by an automated laser device such as a Microtrac X100.

Preferably, the fluidised bed has a particle density of at least 0.6 g/cm$^3$. Catalyst for the production of vinyl acetate may have a density in the range 1.1 to 1.5 g/cm$^3$. Catalyst for the oxidation of ethane and/or ethylene suitably may have a density in the range 1.25 to 3.5 g/cm$^3$, preferably in the range of 1.75 to 2.25 g/cm$^3$. Suitably, the fluidised bed has a settled bed density of at least 0.4 g/cm$^3$.

Suitable catalysts for use in the present invention include oxidation, ammoxidation and carboxylation catalysts.

A catalyst suitable for use in the production of vinyl acetate by the acetoxylation of ethylene may comprise a Group VIII metal, a catalyst promoter and an optional co-promoter. The catalyst may be prepared by any suitable method, such as that described in EP-A-0672453. The Group VIII metal is preferably palladium. The Group VIII metal may be present in a concentration of greater than 0.2% by weight, preferably greater than 0.5% by weight based upon total weight of catalyst. The metal concentration may be as high as 10% by weight. Suitable promoters include gold, copper, cerium or mixtures thereof. A preferred promoter is gold. The promoter metal may be present in an amount of from 0.1 to 10% by weight in the finished catalyst. Suitable co-promoters include Group I, Group II, lanthanide or transition metals, for example selected from the group consisting of cadmium, barium, potassium, sodium, manganese, antimony, lanthanum and mixtures thereof, which are present in the finished catalyst as salts, e.g. an acetate salt. The preferred salts are potassium or sodium acetate. The co-promoter is preferably present in the catalyst composition in a concentration of 0.1 to 15% by weight of catalyst, more preferably, from 1 to 5% by weight. When a liquid acetic acid feed is used, the preferred concentration of co-promoter salt is up to 6% by weight, especially 2.5 to 5.5%. Where the acid is introduced in the vapour phase the co-promoter salt is preferably present in a concentration up to 11 wt %.

A catalyst composition suitable for the selective oxidation of ethane and/or ethylene to acetic acid is described in EP-A-

1069945, the contents of which are hereby incorporated by reference. This describes a catalyst composition comprising in combination with oxygen the elements:—

wherein X is the elements Nb and V;

Y is one or more elements selected from the group consisting of:

Cr, Mn, Ta, Ti, B, Al, Ga, In, Pt, Zn, Cd, Bi, Ce, Co, Rh, Cu, Au, Fe, Ru, Os, K, Rb, Cs, Mg, Ca, Sr, Ba, Zr, Hf, Ni, P, Pb, Sb, Si, Sn, Ti, U, Re and Pd;

a, b, c, d, e and f represent the gram atom ratios of the elements such that
$0 < a \leq 1$, $0 \leq b < 1$ and $a+b=1$;
$0 < (c+d) \leq 0.1$;
$0 < e \leq 2$; and
$0 \leq f \leq 2$.

Another catalyst composition suitable for the oxidation of ethane to ethylene and/or acetic acid and/or for the oxidation of ethylene to acetic acid is described in EP-A-1043064, the contents of which are hereby incorporated by reference. This describes a catalyst composition comprising in combination with oxygen the elements molybdenum, vanadium, niobium and gold in the absence of palladium according to the empirical formula:

wherein Y is one or more elements selected from the group consisting of: Cr, Mn, Ta, Ti, B, Al, Ga, In, Pt, Zn, Cd, Bi, Ce, Co, Rh, Ir, Cu, Ag, Fe, Ru, Os, K, Rb, Cs, Mg, Ca, Sr, Ba, Zr, Hf, Ni, P, Pb, Sb, Si, Sn, Tl, U, Re, Te, and La;

a, b, c, d, e and f represent the gram atom ratios of the elements such that:
$0 < a \leq 1$; $0 \leq b < 1$ and $a+b=1$;
$10^{-5} < c \leq 0.02$;
$0 < d \leq 2$;
$0 < e \leq 1$; and
$0 \leq f \leq 2$.

BRIEF DESCRIPTION OF THE DRAWINGS

The invention will now be illustrated by reference to the following examples and FIGS. 1 to 4 in which.

DETAILED DESCRIPTION OF THE PREFERRED EMBODIMENTS

Apparatus

X-Ray Equipment

Figure 1:
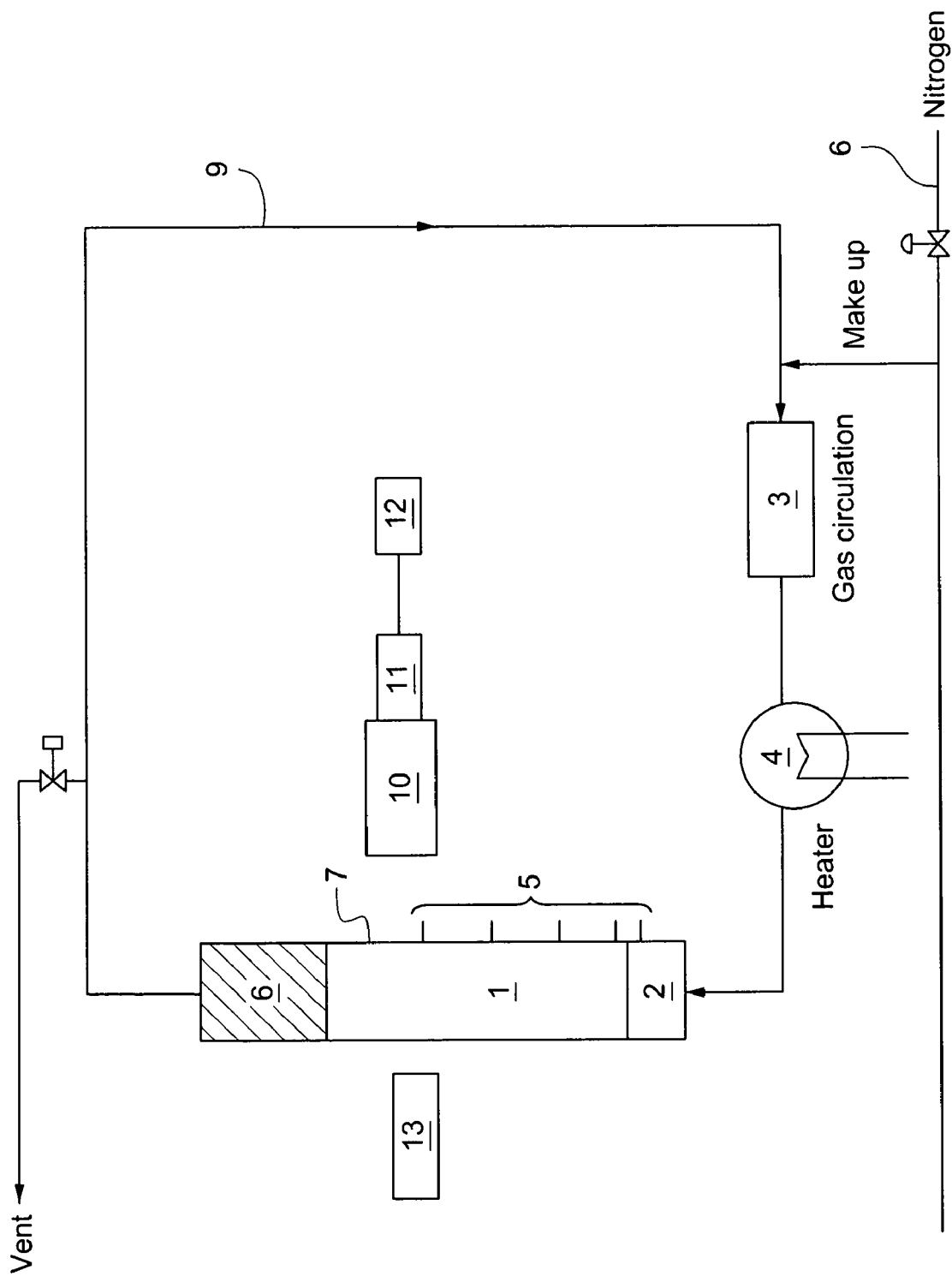
FIG. 1 represents in schematic form apparatus for measuring the fluidisation characteristics of a fluid bed reactor by X-ray imaging.

A series of experiments were performed to study the fluidisation characteristics of a fluid bed using the apparatus shown schematically in FIG. 1. The fluid bed was fluidised with inert gas (nitrogen) rather than reactant gases to enable the fluidisation characteristic of the bed to be studied. Referring to FIG. 1, the apparatus comprised a 420 mm ID aluminium vessel (7), a gas feed system (8) and recycle gas system (9). The vessel contained a bed (1) of fluidisable solid particles supported on a distributor plate (2) through which fluidising nitrogen gas was passed from the gas feed (8) and recycled systems (9) was fluidised with nitrogen from a distributor grid plate (2). The vessel was connected to a positive displacement gas circulation pump (3), heater (4) and gas metering/measuring system (not shown) in a pressurised closed loop. Pressure tappings (5) were positioned along the vessel wall to allow the bulk density of slices of the bed to be derived from the differential pressure across portions of the fluid bed. A section at the top of the bed (6) contained cyclones to prevent solid particles escaping the vessel.

An X-ray gun (13) provided x-rays which passed through the vessel to image intensifier (10), camera (11) and image processing equipment (12).

Supported vinyl acetate catalysts were used in the experiments and were prepared as follows:

a) Preparation of Catalyst Support

The support used for the catalyst preparation was prepared by spray-drying a mixture of Nalco (Nalco Chemical Company) silica sol 1060 and Degussa (Degussa Chemical Company) Aerosil® silica. In the dried support, 80% of the silica came from the sol and 20% of the silica came from the Aerosil. The spray-dried microspheres were calcined in air at 640° C. for 4 hours. This method of support preparation is described in EP-A-0672453.

The particle size distribution of the support which was used for the catalyst preparation is as follows:

| Particle size | % |
|---|---|
| >300 microns | 2 |
| 88-300 microns | 30 |
| 44-88 microns | 38 |
| <44 microns | 30 | b) Preparation of Catalyst A

Silica support (54.4 kg) prepared as hereinbefore described was impregnated with a solution of $Na_2PdCl_4 \cdot xH_2O$ (containing 1 kg palladium) and $AuCl_4 \cdot xH_2O$ (containing 400 g gold) in distilled water by the incipient wetness. The resulting mixture was mixed thoroughly, left to stand for 1 hour and dried overnight.

The impregnated material was added slowly to a 5% solution of hydrazine in distilled water, and the mixture allowed to stand overnight with occasional stirring. Thereafter the mixture was filtered and washed with 4×400 L distilled water. The solid was then dried overnight.

The material was impregnated with an aqueous solution of potassium acetate (2.8 kg) by incipient wetness. The resulting mixture was mixed thoroughly, left to stand 1 hour and dried overnight.

The resulting catalyst comprised 1.6 wt % palladium, 0.6 wt % gold and 5 wt % potassium on silica based on ICP analysis.

Several batches of catalyst were made according to this method and combined. The catalyst was then screened to generate specific size distributions as shown in Table 1.

TABLE 1

|  | Sample 1 | Sample 2 | Sample 3 | Sample 4 |
|---|---|---|---|---|
| <45 microns | 10% | 15% | 20% | 25% |
| 45-111 microns | 80% | 77% | 76% | 72% |
| >111 microns | 10% | 8% | 4% | 3% | c) Preparation of Catalyst B

Prior to use silica support prepared as hereinbefore described was classified to reduce the amount of particles of <45 microns to less than 15%. The silica support (1124 kg) was impregnated with a solution of $Na_2PdCl_4 \cdot xH_2O$ (containing 11.4 kg palladium) and $AuCl_4 \cdot xH_2O$ (containing 4.56 g gold) in distilled water by the incipient wetness technique. The resulting mixture was mixed thoroughly and dried in a ribbon blender with a mean wall temperature of 120° C. During the drying, a dry air purge was passed through the blender over the agitated material to remove the evolved moisture. Following drying the material was cooled to less than 35° C. The impregnated salts were reduced to metallic state by addition of the solid material to a stirred aqueous solution of hydrazine (2200 litres, 5% by weight hydrazine). Thereafter, the material was then pumped to a Nutsche pressure filter and filtered under nitrogen. The filter cake was washed 3 times with about 1000 litres of demineralised water in each wash.

The wet material (filter cake) was blended with solid anhydrous potassium acetate (60 kg) in a ribbon blender and thereafter dried under agitation by introducing steam into the steam jacket of the blender to give a mean wall temperature of 120° C. The evolved moisture was removed with a dry air purge through the blender. Drying was stopped when the moisture content of the material was in the range 20 to 25% by weight. The partially dried material was transferred to a fluid bed drier operated at an air inlet temperature of 150° C. to remove the remaining moisture and give a free flowing catalyst material.

The resulting catalyst comprised 0.93 wt % palladium, 0.37% gold and 2.11 wt % potassium based on ICP analysis.

The particle size distribution of the finished material was as follows:

| Particle size | % |
|---|---|
| >110 microns | 23 |
| 45-110 microns | 68 |
| <45 microns | 9 | c) Fluidisation Experiments (i) Effect of Fines on Fluid Bed Density and Effect of Fluidising Gas Velocity on the Fluid Bed Bulk Density.

90 kg of catalyst A prepared as hereinbefore described was loaded into the aluminium vessel and fluidised with nitrogen at 8 barg and 150-157° C. over a range of gas velocities. Steady state experiments were run (with the cyclones returning any catalyst which reaches the top of the vessel to the catalyst bed). Differential pressure readings were taken from which average bed densities were calculated. The results are shown in Table 2 and plotted in graph form in FIGS. 2 and 3.

TABLE 2

VARIATION OF BED DENSITY[a] WITH FINES CONTENT AND VELOCITY

|  | Velocity = 13 cm/s | Velocity = 17 cm/s | Velocity = 21 cm/s |
|---|---|---|---|
| 10% <45 micron[b] | 459 | 424 | 395 |
| 15% <45 micron[b] | 409 | 432 | 409 |
| 20% <45 micron[b] | 375 | 303 | 239 |
| 25% <45 micron[b] | 332 | 294 | 245 |

[a]Bed density (in $kg/m^3$) is the average of two density measurements made in the first 1.0 m of the fluid bed (measured from the grid plate upwards).
[b]Fines (defined as <45 micron material) content of the catalyst as loaded into the reactor.

Figure 2:
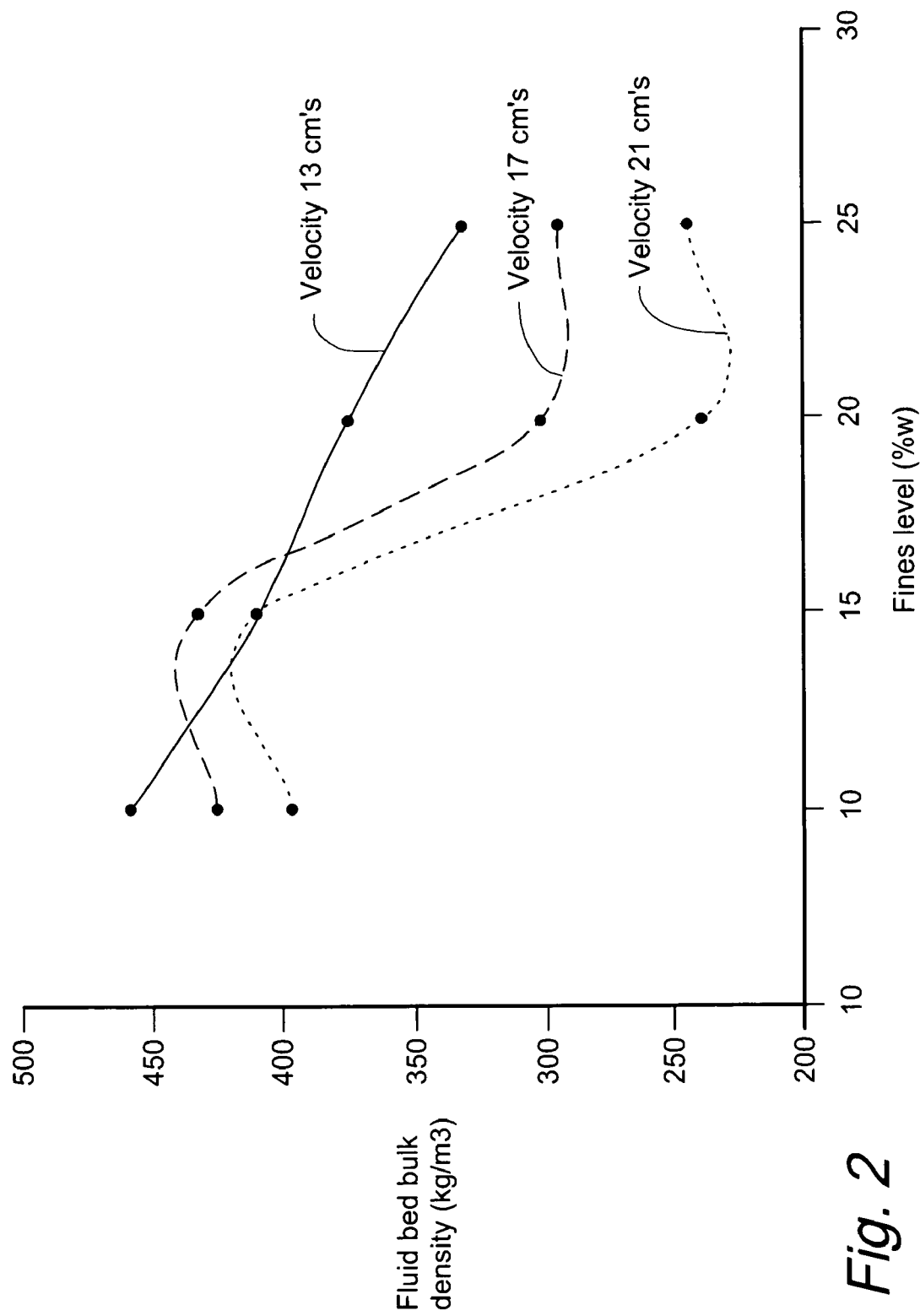
FIG. 2 represents in graph form the effect of the level of fines in the fluid bed on the fluid bed density.
Figure 3:
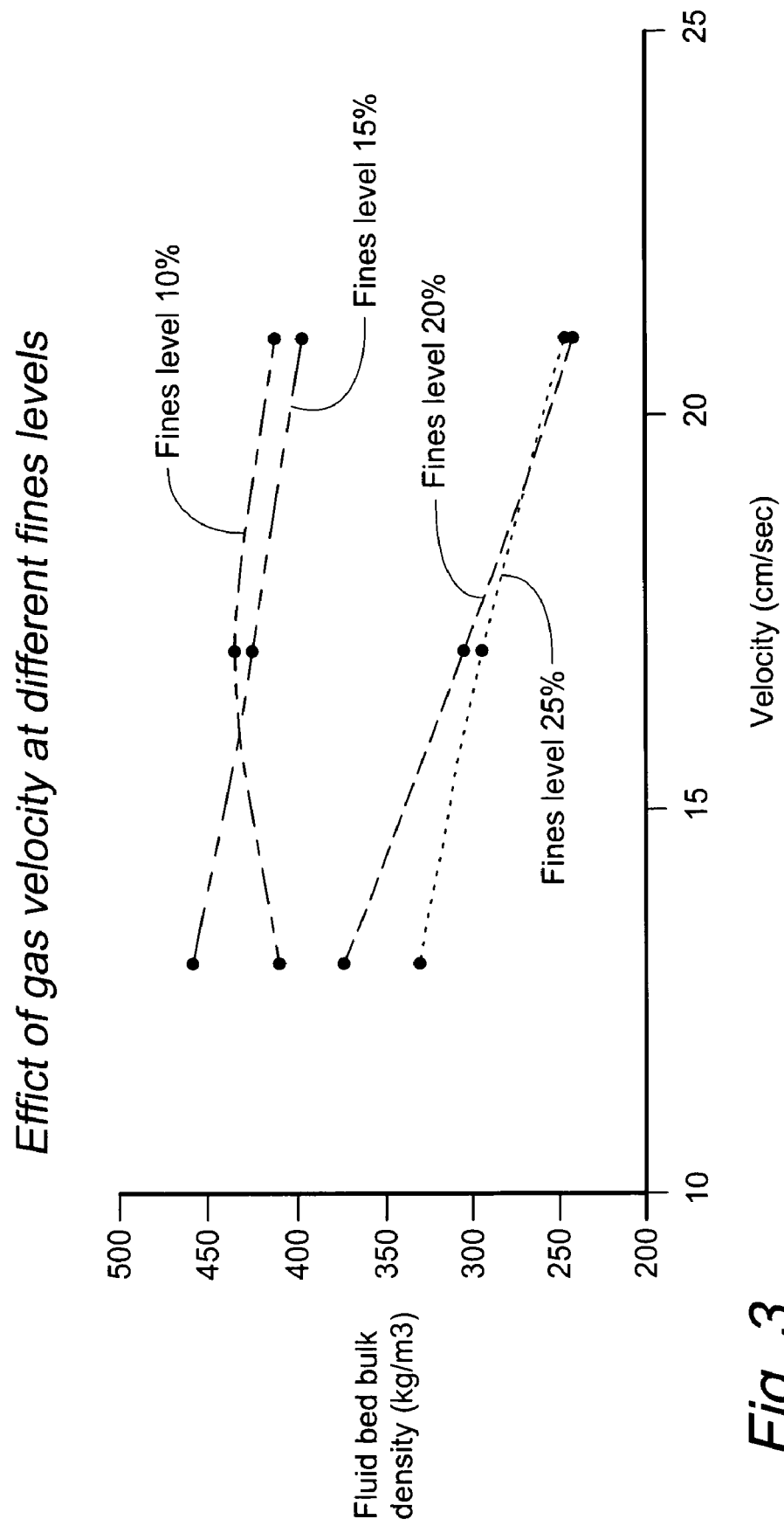
FIG. 3 represents in graph form the effect of fluidising gas velocity on the fluid bed bulk density and FIG. 4 represents in graph form the effect of ethylene on the fluid bed density.

The velocity in Table 2 and in FIGS. 2 and 3 is the superficial gas velocity of the fluidising gas and is defined as gas flow rate ($cm^3/s$)/fluid bed cross-section area ($cm^2$).

During these experiments, the x-ray images showed that the bed was being maintained in a turbulent regime. Thus, the experiments show that there is a range of operating conditions under which a turbulent regime can be maintained.

Referring to FIG. 2, this shows the bed density as a function of the amount of fines in the fluid bed at three different superficial velocities. The data show that as the superficial gas velocity is increased, the bed density decreases. Also, at any given superficial gas velocity, as the amount of fines increases so the bed density decreases. There is a sharp reduction in bed density at the higher fines content (>20%) and high gas velocity (>21 $cm^3/s$) indicating that the bed is entering the transport regime, where it occupies all the available space in the vessel.

Referring to FIG. 3, this shows the bed density as a function of the superficial gas velocity for the different amount of fines in the fluid bed. The data show that as the superficial gas velocity is increased, the bed density decreases. There is a reduction in bed density as the fines content increases, particularly at high gas velocity (>21 $cm^3/s$). This indicates that the level of fines should be kept at no greater than 15% to maintain a reasonable bed density and prevent transportation at the higher gas velocity.

(ii) Effect of Ethylene on the Fluid Bed Density 5.1 kg of catalyst B prepared as hereinbefore described was loaded into a 2.1 metre tall vessel with a diameter of 3.5 inches. At the top of the vessel a cone shaped expansion section was fitted followed by a straight sided freeboard section with a diameter of 6 inches. The vessel was equipped with a differential pressure transmitter covering the lower 1.38 metres of height. Thus based on the known volume of the lower section of the vessel and the mass of catalyst in that section from the differential pressure transmitter reading the density of the fluidised bed could be calculated. Two experiments were carried out. The first experiment used nitrogen as fluidising gas. The second experiment used ethylene with 10-20 vol % nitrogen as fluidising gas. The experiments were carried out at 154° C. and at a pressure range of 7.2 to 9.2 barg.

Figure 4:
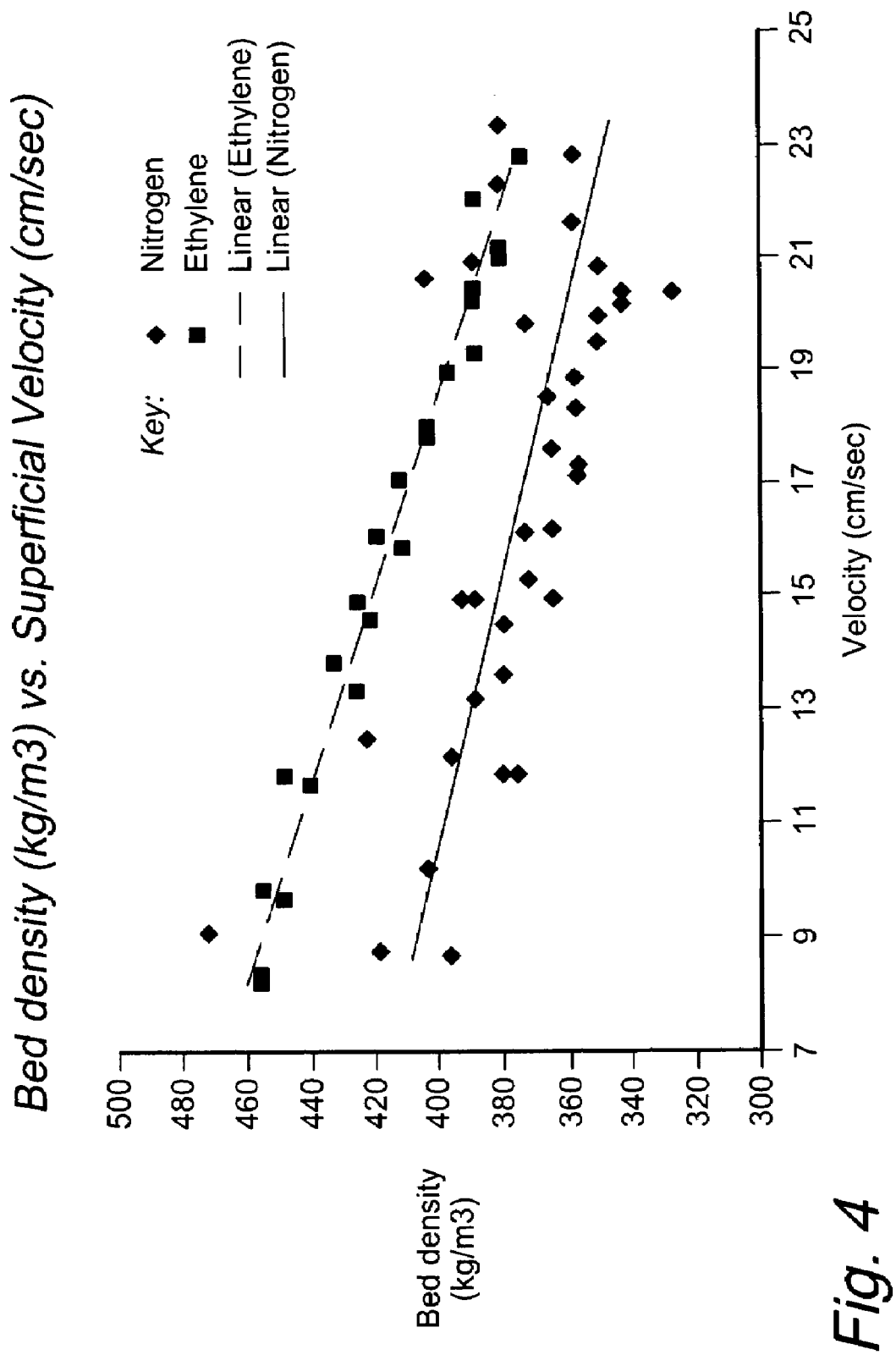

Referring to FIG. 4, this shows the bed density as a function of the superficial gas velocity for the different fluidizing gases. The data shows a higher bed density is achieved when ethylene is used as a fluidising gas compared to the bed density achieved when nitrogen is used as the fluidising gas. The data also indicates that higher superficial gas velocities may be achieved when using ethylene as the fluidising gas whilst still in the turbulent regime. It is believed that the increased noise in the nitrogen data above 19.5 c m/sec is due to the bed transporting.

Further experiments were performed to investigate the effect of bed density on the fluidisation characteristics.

Effect of Bed Density on Fluidisation.

Catalysts containing a densifier were prepared and tested as follows.

a) Preparation of Support

EXAMPLES

Example 1 (Comparative)

The support was prepared by spray-drying a mixture of Nalco (Nalco Chemical Company) silica sol 1060 and Degussa (Degussa Chemical Company) Aerosil® silica. In the dried support, 80% of the silica came from the sol and 20% of the silica came from the Aerosil. The spray-dried microspheres were calcined in air at 640° C. for 4 hours. This method of support preparation is described in EP-A-0672453.

Example 2

The support was prepared as in Example 1 except that 90% of the silica came from the sol and 10% came from the Aerosil Example 3

The support was prepared as in Example 2 except that the Aerosil was replaced by tin oxide.

The particle size distributions of the supports are as follows:

| Particle size | % Example 1 | % Example 2 | % Example 3 |
|---|---|---|---|
| >350 microns | 0.8 | 0.3 | 0 |
| 88-350 microns | 27.4 | 15.1 | 12.5 |
| 40-88 microns | 33.8 | 31.5 | 31.5 |
| <40 microns | 38.0 | 53.1 | 56.0 | b) Preparation of Catalyst 30.0 g of microspheroidal support was impregnated with a solution of $Na_2PdCl_4 \cdot xH_2O$ (1.84 g, 28.9% Pd) and $HAuCl_4 \cdot xH_2O$ (0.44, 49.0% Au) in distilled water (20.0 cm$^3$) by incipient wetness. The resulting mixture was mixed thoroughly, left to stand for 1 hour and then dried overnight.

The impregnated material was allowed to cool to room temperature, and then was added to a solution of hydrazine (3.0 g of a 55% aqueous solution of $N_2H_4$) in 80.0 cm$^3$ distilled water, and the mixture allowed to stand overnight with occasional stirring. Thereafter the mixture was filtered and washed with 4×250 cm$^3$ distilled water. The solid was then dried overnight.

The material was impregnated with an aqueous solution of potassium (1.64 g) by incipient wetness. The resulting mixture was mixed thoroughly, left to stand for 1 hour and dried overnight.

The catalyst of Example 1 had a metal loading of 1.49% Pd, 0.44% Au and 3.64% potassium acetate. The catalyst of Example 2 had a metal loading of 1.65% Pd, 0.53% Au and 4.54% potassium acetate. The catalyst of Example 3 had a metal loading of 1.63% Pd, 0.54% Au and 4.49% potassium acetate, 0.47% Sn.

c) Production of Vinyl Acetate

The catalysts were tested in a bench scale fluid bed reactor with a maximum catalyst capacity of 40 cm$^3$. For each experiment 30 cm$^3$ of catalyst-plus-diluent was loaded into the reactor. Typically 2 g of catalyst was used. The inert diluent consisted of silica loaded with gold and potassium acetate. The reactor was equipped with two feed inlets. Ethylene, acetic acid, and oxygen all entered the reactor through a lower inlet and nitrogen only was fed through the second inlet which was located 2.5 inches above the first.

The reactor pressure was controlled at 8 barg and all lines leading to and from the reactor were heat traced and maintained at 150-160° C. in order to prevent condensation of liquid feeds or products. The reactor was normally maintained at a temperature of 150-160° C.

The gaseous reactor effluent was analysed on-line using a Hewlett Packard Model 5890 gas chromatograph equipped with both TCD and FID detectors. Oxygen, nitrogen, ethylene and carbon dioxide were separated on a 13× mole sieve column parallel with 10% Carbowax 20M on 80/100 Chromosorb WAW and 23% SP2700 on 80/100 Chromosorb PAW, and quantified with the TCD. Vinyl acetate and acetic acid and other organic by-products were separated on a J&W DB 1701 megabore capillary column and quantified with the FID. Data was analysed via a customised Excel spreadsheet.

| Example | Settled Bulk Density of Support g/cm$^3$ | Catalyst Activity gVA/kg-cat/hr | Selectivity |
|---|---|---|---|
| Example 1 run 1 | 0.66 | 1420 | 91.8 |
| Example 1 run 2 | 0.66 | 1270 | 93.1 |
| Example 2 | 0.80 | 1280 | 90.6 |
| Example 3 run 1 | 0.94 | 1270 | 89.4 |
| Example 3 run 2 | 0.94 | 1200 | 92.8 |

The data show that catalysts with higher densities can be made by adding inert oxides during support preparation, and such catalysts have similar intrinsic activity to catalysts made without a densifier. Thus, in view of the fluidisation experiments, it can be concluded that increasing the density of the fluid bed solid particles, for example by using a densifier, may enable higher superficial gas velocities to be used and/or higher levels of fines whilst maintaining the fluid bed in a turbulent, non-transporting regime.

We claim:

1. A process for reacting in a fluid bed reactor, at least one oxidisable hydrocarbon reactant which is not ethane or ethylene or propylene with molecular oxygen in the presence of a catalytically active fluidised bed of solid particles, which process comprises introducing a molecular oxygen-containing gas having an oxygen concentration greater than that of air into said fluidised bed whilst said fluidised bed is maintained in a turbulent regime, wherein the turbulent regime has the ratio of transition velocity ($U_k$):terminal velocity ($U_t$) in the range 0.1:1 to 25:1.

2. A process according to claim 1 wherein the hydrocarbon is a $C_4$ hydrocarbon and the $C_4$ hydrocarbon is reacted with molecular oxygen to produce maleic anhydride.

3. A process according to claim 1 wherein the hydrocarbon is reacted with molecular oxygen and ammonia.

4. A process according to claim 3 wherein the hydrocarbon is propane, and the hydrocarbon is reacted with molecular oxygen and ammonia to produce acrylonitrile.

5. A process according to claim 1 wherein the solid particles have a particle diameter in the range 20 to 300 microns.

6. A process according to claim 3 wherein the particle diameter size distribution is at least 20 microns.

7. A process according to claim 1 wherein the fluidised bed comprises solid particles having sizes according to one or more of the following independent criteria: (i) at least 65% of the particles have particle diameters in the range 20-120 microns; (ii) less than 15% of the particles have a particle diameter less than 45 microns; and (iii) less than 5% of the particles have a particle diameter greater than 105 microns.

8. A process according to claim 1 wherein the concentration of oxygen in the molecular oxygen-containing gas is in the range 50 to 100% by volume.

9. A process according to claim 1 wherein the at least one oxidisable reactant is introduced into the fluidised bed as a gas and/or liquid through one or more inlets.

10. A process according to claim 9 wherein the at least one oxidisable reactant is introduced into the fluidised bed as a gas and is a component of the fluidising gas.

11. A process according to claim 1 wherein the fluidised bed has a particle density of at least 0.6 g/cm$^3$.

12. A process according to claim 1 wherein the fluidised bed has a settled bed density of at least 0.4 g/cm$^3$.

13. A process according to claim 1 wherein the solid particles comprise a support.

14. A process according to claim 13 wherein the support is selected from the group consisting of silica, alumina, silica/alumina, titania, silica/titania, zirconia and mixtures thereof.

15. A process according to claim 1 wherein the particle density of the solid particles is modified by the use of a densifier during the preparation of the particles.

16. A process according to claim 15 wherein the densifier is used during preparation of the support.

17. A process according to claim 16 wherein the densifier is an inert oxide.

18. A process according to claim 17 wherein the inert oxide is tin oxide.

19. A process according to claim 16 wherein the particle density is modified by substitution of at least one metal of the solid particles by at least one metal having a higher atomic weight.

20. A process according to claim 19 wherein the at least one substituting metal is chemically equivalent to the at least one substituted metal.

21. A process according to claim 20 wherein the solid particles comprise at least one of Mo, V and Nb, and the particle density of the particles is modified by substituting at least one of Mo, V, Nb by at least one of Sn, Te, La, Ta, W, Re, Pb, Bi, Ce, Pr, Gd and Yb.

22. A process according to claim 1 wherein the particle density of the solid particles is modified by the use of a fluidising gas.

* * * * *